United States Patent [19]

Regnier et al.

[11] 4,108,603
[45] Aug. 22, 1978

[54] METHOD FOR RAPID ANALYSIS OF HEMOGLOBIN VARIANTS BY HIGH SPEED LIQUID CHROMATOGRAPHY

[75] Inventors: Frederick E. Regnier, West Lafayette, Ind.; Shung-Ho Chang, St. Louis, Mo.

[73] Assignee: Purdue Research Foundation, West Lafayette, Ind.

[21] Appl. No.: 798,135

[22] Filed: May 18, 1977

[51] Int. Cl.² .................. G01N 31/08; G01N 33/16
[52] U.S. Cl. ............................. 23/230 B; 210/31 C; 424/101
[58] Field of Search .................. 23/230 B; 210/31 C; 424/101

[56] References Cited

PUBLICATIONS

Chemical Abstracts, 83:55371r, (1975).
S. Chang et al., Anal. Chem., 48(13), 1839–1845 (1976).

*Primary Examiner*—Sidney Marantz
*Attorney, Agent, or Firm*—John R. Nesbitt

[57] ABSTRACT

A method for analysis of hemoglobin variants by high speed liquid chromatography and, more particularly, by ion-exchange chromatography. Through the use of high flow rates and pressures, the hemoglobin variants can be rapidly forced through the separation column to thus enable rapid analysis. A bonded phase inorganic support column is utilized for separation of the hemoglobin variants with the profiles thereof then being obtained. The bonded phase support preferably includes ion-exchange groups bonded through a carbohydrate intermediate to controlled porosity glass. A pair of different columns may be utilized to separate the hemoglobin variants with one of the columns being an anion-exchanger, and more particularly, a diethylaminoethanol glycophase, controlled porosity glass column, with the other column being a cation-exchanger, and more particularly, a carboxymethyl glycophase, controlled porosity glass column. The hemoglobin profiles obtained from such a pair of columns are different and the combination of chromatographic data obtained identify the particular hemoglobin variants and can thus be utilized for diagnosis purposes.

18 Claims, 4 Drawing Figures

METHOD FOR RAPID ANALYSIS OF HEMOGLOBIN VARIANTS BY HIGH SPEED LIQUID CHROMATOGRAPHY

FIELD OF THE INVENTION

This invention relates to a method for analysis of hemoglobin variants, and more particularly, relates to a method utilizing high speed liquid chromatography for rapid analysis of hemoglobin variants.

BACKGROUND OF THE INVENTION

The analysis of hemoglobin variants is important to the health of many people. For example, the presence of certain abnormal hemoglobins is indicative of hematological disease or the possibility of transmitting such a disease to an offspring. While it is believed that there is no known cure for hemoglobinopathies, early diagnosis can enable a physician to take proper precautions as, for example, during pregnancy or surgery, as well as to recognize clinical manifestations. In addition, persons with the disease, or traits thereof, can be better informed of the genetic implications where diagnosis has occured.

While various methods and/or systems have been developed heretofore to obtain an analysis of hemoglobin variants, improvements in such methods and/or systems are believed to be needed, particularly in providing a rapid method for analysis that is also necessarily accurate. Present methods and/or systems are discussed hereinafter with respect to the various types of hemoglobins and/or abnormalities. In addition, a review of the structure of hemoglobins and its abnormalities may be found, for example in *Blood and Its Disorders*, Blackwell Scientific, Oxford (1974).

SUMMARY OF THE INVENTION

This invention provides a method for rapid and accurate analysis of hemoglobin variants by high speed liquid chromatography. One or more bonded phase inorganic support columns are provided to separate the hemoglobin variants after which the hemoglobin profiles are obtained. Ion-exchange chromatography is utilized with an anion-exchanger and a cation-exchanger providing different hemoglobin profiles which when combined establish relative quantities of the hemoglobin variants for diagnosis purposes.

It is therefore an object of this invention to provide an improved method for analysis of hemoglobin variants.

It is another object of this invention to provide an improved method for analysis of hemoglobin variants by high speed liquid chromatography.

It is still another object of this invention to provide an improved method for analysis of hemoglobin variants by high speed liquid chromatography that is rapid and yet accurate.

It is yet another object of this invention to provide an improved method for analysis of hemoglobin variants by ion-exchange chromatography.

It is still another object of this invention to provide an improved method for analysis of hemoglobin variants by ion-exchange chromatography utilizing a bonded phase inorganic support.

It is yet another object of this invention to provide an improved method for analysis of hemoglobin variants by ion-exchange chromatography that includes an anion-exchanger and a cation-exchanger.

It is still another object of this invention to provide an improved method for analysis of hemoglobin variants that includes obtaining the profiles of the hemoglobin variants and determining therefrom relative quantities for diagnosis purposes.

With these and other objects in view, which will become apparent to one skilled in the art as the description proceeds, this invention resides in the novel method substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate profiles obtained from a complete embodiment of the invention according to the best mode so far devised for the practical application of the principles thereof, and in which.

DESCRIPTION OF THE INVENTION

Figure 1:
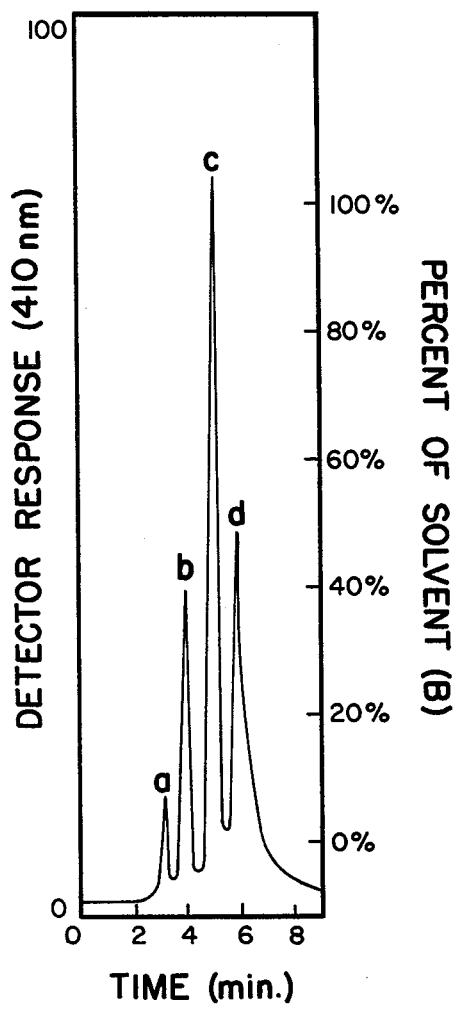
FIG. 1 is a hemoglobin profile showing resolution of a hemoglobin control sample utilizing a DEAE Glycophase/CPG column.

Hemoglobin is a tetrameric protein composed of two pairs of identical chains (globins) each of which is attached to a heme group. In the course of the life of normal individuals, combinations of five different globin chains ($\alpha, \beta, \gamma, \delta$ and $\epsilon$) occur. In the first few weeks of life, embryonic hemoglobins Hb-Gower 2 ($\alpha_2\epsilon_2$), Hb-Gower 1, and Hb-Portland ($\delta_2\gamma_2$) are present. The $\epsilon$ chains disappear by the end of the first trimester so Hb-Gower 1 and Hb-Gower 2 are not found in infants. Hb-Portland has been found, but is is difficult to separate from Hb-A so it has not been extensively studied as regards disappearance. The fetal hemoglobin Hb-F ($\alpha_2\gamma_2$) appears at about the tenth week of gestation and survives until at least several months past birth. Hb-$F_1$ is Hb-F with the terminal amino groups of the $\gamma$ chains blocked and is usually present with Hb-F. Hb-Bart's ($\gamma_4$) is also present in very small amounts (0.2–0.3% of the total hemoglobin) at birth in normal babies. Hb-A ($\alpha_2\beta_2$) is the hemoglobin found in normal adults (96–99% of the total hemoglobin) with 1.5–3.2% Hb-$A_2(\alpha_2\beta_2)$.

Since 8% of the black population in the U.S. carry the sickle cell trait and about 0.2% have sickle cell disease, it is important to be able to determine Hb-S ($\alpha_2\beta_2^{6Glu \rightarrow Val}$). Sickle cell disease occurs in people homozygous for Hb-S. Sickle cell disease has many clinical manifestations including crises caused by multiple small infarctions. Sometimes the disease does not show until pregnancy or surgery when serious complications can arise. Pregnancy is accompanied by high rates of fetal and maternal mortality. Sickle cell trait, the heterozygous state, has few, it any, clinical problems. Its major importance is the genetic probability of having children with either sickel cell disease or a sickle cell combination with another abnormality. It is important to distinguish sickle cell disease from sickle cell trait for sociological reasons. People with the disease are restricted as to air travel and duty in the armed forces. At high altitudes, Hb-S, which has a low affinity for oxygen, has a tendency to sickle and cause hypoxia, especially in unpressurized aircraft. Those people with sickle cell traits have Hb-A in addition to Hb-S so they should not be subject of these limitations.

Hb-S is usually determined by both electrophoresis and a solubility test. Cellulose acetate electrophoresis is the generally accepted clinical method with quantitation by densitometry. The solubility test is based on the fact that Hb-S is insoluble in a buffered salt solution containing a reducing agent, yielding a cloudy mixture. Both tests together give precise results although lack of proficiency or experience can give false positives since Hb-D and Hb-G migrate similarly to Hb-S.

About 3% of the black population of the U.S. have the Hb-C ($\alpha_2\beta_2^{6Glu\rightarrow Lys}$) trait. Neither the heterozygous nor the homozygous form is particularly dangerous, but a combination of Hb-S and Hb-C can be problematic. There are few clinical manifestations so it often goes undetected and crises can occur in pregnancy, during surgery, or under severe stress.

Hb-C and Hb-$A_2$ cannot be resolved by cellulose acetate electrophoresis as routinely performed. They are resolved by chromatography on carboxymethyl (CM) cellulose. Alternatively, electrophoresis has been used to separate and identify the dissociated globin chains of electrophoretically similar hemoglobins.

Hb-E ($\alpha_2\beta_2^{26Glu\rightarrow Lys}$) is the second most common hemoglobin in the world-present in people of South East Asian origin. In the homogzygous state there is mild anemia. Occasionally other mild clinical signs are present.

There are other abnormal hemoglobins and variants such as Hb-M, Hb-D and Hb-G which occur infrequently. Some cause disease but many do not. It is important to be aware of these since they may interfere in the identification of other hemoglobins. For example, Hbs-S, D, G and P are electrophoretically similar as are Hbs-$A_2$, C, E and O.

There are two types of $\beta$-thalassemia. In one, the production of $\beta$-chain is turned off and in the other, it is limited. Someone who is homozygous for either condition has Cooley's anemia. Cooley's anemia is characterized by severe anemia, splenomegaly, hepatomegaly and skeletal deformities with many possible complications. This disease is usually fatal. Patients rarely reach their twenties and die from accumulation of iron in the heart. Only Hb-F and Hb-$A_2$ are present if there are no $\beta$-chains. With reduced synthesis, some Hb-A is also present. The diagnostic value of the Hb-$A_2$ level is questionable because of its variability which is complicated by the heterogeneity of Hb-F in the cells. It has also been suggested that Hb-$A_2$ levels greater than 600 mg/100 ml imply $\beta$-thalassemia. In 1972, the National Cooley's Anemia Control Act was passed which provides for screening, treatment and counseling programs for Cooley's anemia. Little has been done to implement this due to problems in methodology. Densitometry, the method of quantitation with cellulose acetate electrophoresis, has been found to be inexact. DEAE ion-exchange chromatography is preferred but felt to be too slow. Methods have been developed to determine Hb-$A_2$ by a batch assay using DEAE bioGel A and by microchromatography with DEAE cellulose. Both of these studies are attempts to speed up the chromatographic process.

Heterozygous $\beta$-thalassemia or thalassemia minor is asymptomatic except for mild anemia which is particularly noticeable during pregnancy or times of stress. This is often confused with iron deficiency anemia and as such is improperly treated with iron instead of folic acid. In thalassemia minor, Hb-$A_2$ levels are raised to 3.5-7.5% and in about half the patients, Hb-F is present up to about 4%. The children of these people could be seriously ill if the other parent has a gamete for Hb-S, Hb-E or $\beta$-thalassemia.

In $\delta\beta$-thalassemia, the synthesis of $\delta$ and $\beta$ chains is completely repressed, so that in the homozygous state only Hb-F is present. It is similar to Cooley's anemia clinically but is somewhat milder. The heterozygous state has Hb-F levels of 5-15%, Hb-$A_2$ slightly below normal, and primarily Hb-A. People who are heterozygous for both $\beta$- and $\delta\beta$-thalassemia have symptoms like mild Cooley's anemia. The Hb-F constitutes 90-95% of the total hemoglobin, Hb-$A_2$ levels are normal and occasionally some Hb-A is present. Because of the similarities of many of the $\beta$-thalassemias, a family study often helps to determine which conditions are involved.

There are two kinds of $\alpha$-thalassemia -$\alpha^{thal\ 1}$which stops $\alpha$ chain synthesis and $\alpha^{thal\ 2}$which reduces it. The homozygous state of $\alpha^{thal\ 1}$, *hydrops fetalis*, produces no Hb-F or Hb-A and is incompatible with life. These infants are either stillborn or live only a few minutes. Their blood has 80-90% Hb-Bart's ($\delta_4$) with the remainder Hb-H ($\beta_4$) and Hb-Portland ($\delta_2\gamma_2$). Hb-H disease is another homozygous state which is a $\alpha^{thal\ 1}\alpha^{thal\ 2}$or $\alpha^{thal\ 2}\alpha^{thal\ 2}$ combination. The clinical problems range from severe cases similar to Cooley's disease to only minor splenomeglay. In this disease, the Hb-H level is 5-40% and that of Hb-Bart's is somewhat smaller; Hb-A and Hb-$A_2$ are also present as well as occasional free $\delta$ chains and/or Hb-F. Hb-H is unstable and precipitates with oxidizing agents; therefore, many drugs should not be administered to these people. Pregnant patients may need blood transfusions and have folate deficiencies.

It is difficult to diagnose the heterozygous state of $\alpha$-thalassemia. If there are more than 1-2% Hb-Bart's in cord blood, the family history should probably be investigated. Sometimes Hb-H or Hb-Bart's may be present in small amounts in adults but this is not a good diagnostic indication of a $\alpha$-thalassemia trait.

Hemoglobin Constant Spring (Hb-CS) is found in some patients with apparent Hb-H disease. It is an electrophoretically slow-moving hemoglobin with a normal chain extended by 31 extra residues on the C terminus. Hb-CS may be found in 50% of some South East Asian populations. Hb-CS heterozygotes and hemozygotes have a mild form of $\alpha$-thalassemia. Heterozygotes for Hb-CS and $\alpha^{thal\ 1}$have a clinical condition similar to Hb-H disease.

Hb-E and $\alpha$-thalassemia are both very common in South East Asia. Combinations of the traits produce varied clinical states ranging from normal to severe Cooley's anemia. Blood samples from these patients contain significant amounts of Hb-E besides varied amounts of Hb-A, Hb-F and Hb-Bart's.

In Heriditary Persistance of Fetal Hemoglobin (HPFH) Hb-F is homogeneously distributed among the red cells in contrast to other abnormal appearances of Hb-F where it is heterogeneously distributed. No clinical problems are associated with HPTH even in the homozygous state where Hb-F comprises 100% of the total hemoglobin. Because Hb-F protects Hb-S against sickling, people with both traits are in good health.

Certain physiological factors can alter the hemoglobin levels. Iron deficiency and anemia can lower Hb-$A_2$. Pregnancy, leukemia, some anemias, tumors and drugs can increase Hb-F levels. Some forms of malaria might increase Hb-$A_2$.

Methemoglobin is hemoglobin with the bound ferrous ion ($Fe^{2+}$) oxidized to the ferric ion ($Fe^{3+}$). Methemoglobin has no oxygen-carrying capability. Normally methemoglobin comprises about 0.5% of total hemoglobin; however, in congenital methemoglobinemia it comprises 10–20%. These levels are accompanied by cyanosis and often by mental deficiency. Certain chemicals and drugs can cause the formation of methemoglobin which is only harmful in large concentrations. This chemically induced methemoglobin formation is used to detoxify the blood after cyanide poisoning.

Hb-$A_{1c}$ is a variant of Hb-A which is found in most blood but is elevated in persons with diabetes mellitus. It has been found to be acquired rather than genetically caused. Probably it is formed by faulty carbohydrate metabolism since Hb-$A_{1c}$ is Hb-A with bound carbohydrate. Normal levels of Hb-$A_{1c}$ are 4–6% whereas those of diabetic patients are twice as high.

The usual method of determining hemoglobin variants, heretofore, is cellulose acetate electrophoresis followed by densitometric quantitation, and in case of suspected Hb-S, a solubility test is also performed. Using cellulose acetate electrophoresis, Hbs-S, D, G and P cannot be resolved, likewise Hbs-$A_2$, C, E and O are not resolved. Starch gel electrophoresis has similar resolution problems. Agar electrophoresis gives better separations than cellulose acetate, but it is expensive and difficult to use. The separations by paper electrophoresis are not as good as those by other methods but the technique has been implemented. The method of quantitating electrophoretic bands, densitometry, has been shown to lack precision. The inability to separate certain hemoglobins makes electrophoresis imprecise as a qualitative method also.

Hemoglobins which are not resolved by electrophoresis have been differentiated by chain sequencing, identification of composite globin chains, and ion-exchange chromatography. One research group examined chain sequences when they suspected two people of being Hb-S-G and Hb-S-D heterozygotes rather than Hb-S homozygotes as the electrophoresis suggested. Schneider resolved individual globins using a urea-mercaptoethanol buffered hemolysate and both acid and alkaline electrophoresis on cellulose acetate.

Ion-exchange chromatography, on the other hand, has been a good method for separating hemoglobins. Usually ion-exchange supports have been used in column chromatography although DEAE BioGel A has been used in a batch assay to determine Hb-$A_2$. A weak anion-exchanger, diethylaminoethanol (DEAE), bound to cellulose or Sephadex has been used in column chromatography with the latter giving better resolution of hemoglobin variants. DEAE Sephadex separated variants of Hb-F as well as variants of Hb-$A_2$. A weak cation-exchanger, carboxymethyl (CM) cellulose gave much different separations than the DEAE column. On CM-cellulose, Hb-$A_2$ can be separated from Hb-C, some Hb-$A_2$ variants can be resolved and Hb-$A_{1c}$ can be resolved from other Hb-A variants. Although the resolution and quantitation of ion-exchanger chromatography is excellent, the technique using carbohydrate gel supports is very slow, requiring many hours or even days for analysis. Microchromatography on small columns of DEAE cellulose has been used to give a fast determination of Hb-$A_2$. A microcolumn of CM-cellulose was used to differentiate Hb-S from Hb-C. These columns are limited to a rapid determination of some specific variants.

Hemoglobin can be detected and quantitated with a spectrophotometer at about 415 nm. Methemoglobin can similarly be measured at 632 nm and cyanomethamoglobin at 540 nm.

The major limitations of gel supports have recently been overcome by a series of bonded phase inorganic supports as shown and claimed in U.S. Pat. No. 3,983,299 issued to F. E. Regnier and in U.S. patent application Ser. No. 554,071 filed by F. E. Regnier and S. H. Chang on Feb. 28, 1975, U.S. Pat. No. 4,029,583. Ion-exchanger groups are bonded through a carbohydrate intermediate to controlled porosity glass. The carbohydrate layer protects proteins from denaturation by inorganic supports such that enzymes retain their activity after chromatography. These high speed inorganic ion-exchange supports, including DEAE and CM, parallel their gel counterparts in chromatographic protocol but can be run at pressures up to 5000 psi. Gradients and recycling do not damage the supports and columns may be used for many separation cycles. Analyses of protein mixtures on microparticulate supports (5–10 $\mu$) take only 5–20 minutes with a recycle time of several minutes.

It is evident from the foregoing that a substantial segment of the population has abnormal hemoglobins which may affect their health and can be genetically transmitted to their offspring. It is also apparent that the clinical manifestations of the various hemoglobinopathies can be properly diagnosed when the physician is aware of the disease. The problem in diagnosing and managing hemoglobinopathies appears to have a strong analytical component. Electrophoresis is both quantitatively and qualitatively inexact in the determination of abnormal hemoglobin. Ion-exchange chromatography on DEAE and CM carbohydrate gel columns gives excellent resolution and quantitation but it is slow, requires considerable manual manipulation and necessitates pouring a new column after several runs.

The inorganic phase bonded support for high speed liquid chromatography seems to overcome many of the problems of the analytical systems used previously in hemoglobin analysis. First, DEAE and CM may be bonded to rigid supports capable of withstanding high flow rates and pressures. Second, these supports resolve proteins 10–100 times faster than the classical supports. Third, columns packed with the supports may be used through hundreds of sample runs. Fourth, the columns fit into existing high pressure liquid chromatographic instrumentation. Fifth, samples are eluted from these columns directly into highly precise spectrophotometric detectors equipped with recording devices and/or electronic integrators. Sixth, automatic sample injection, solvent programming, column recycling, data acquisition and processing, and reporting in a specified format may be achieved with little operator attention.

The following examples show preparation of columns for use in this invention. Such columns (and similar colums) are shown in more detail in U.S. Pat. No. 3,983,299 and/or allowed U.S. patent application Ser. No. 554,071, filed Feb. 28, 1975.

EXAMPLE I

DEAE Column Preparation

Microparticulate silica or glass with particle diameters of 5–10 μ is prepared as the chromatographic support material. These supports will yield optimum efficiency and thus, resolution. If the ion-exchange coatings are not commercially available on microparticulate glass, the DEAE and CM glycophase/CPG is to be synthesized as follows: First a glycerol monolayer is bonded to the support material by reaction with a 10% aqueous solution of γ-glycidoxypropyltrimethoxysilane.

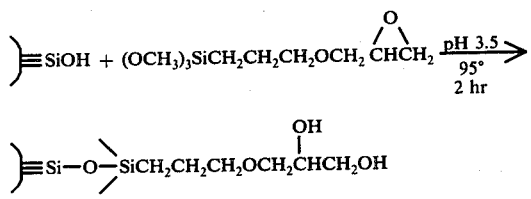

This glycerolpropylsilyl support, called Glycophase G, is then reacted further to make the ion-exchange supports. To prepare the DEAE support, Glycophase G is reacted with triglycidylglycerol and diethylaminoethanol in dimethylformamide. Afterwards, another layer of triglycidylglycerol is coated onto the support and polymerized in a fluidized bed with $BF_3$.

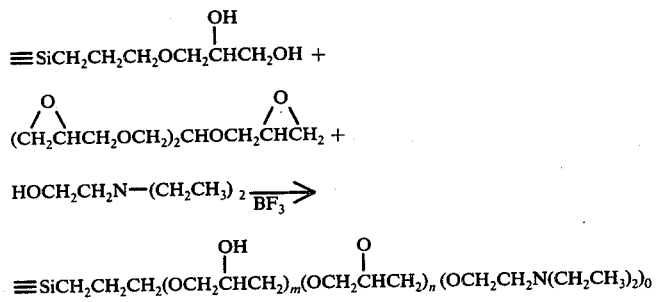

EXAMPLE II

CM Column Preparation

To prepare the CM support, Glycophase G is coated with triglycidylglycerol and polymerized in HCl. The resulting diol support is oxidized with periodate/permanganate to yield the acid.

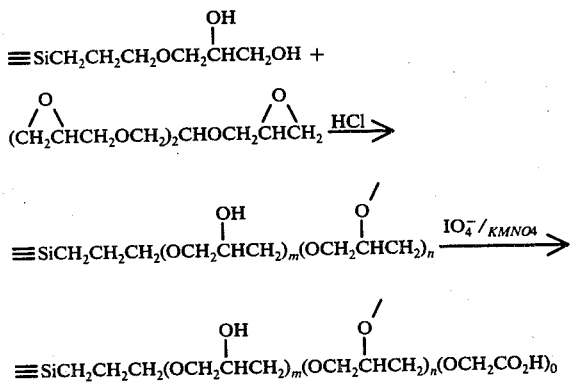

EXAMPLE III

Column Resolution

Figure 2:
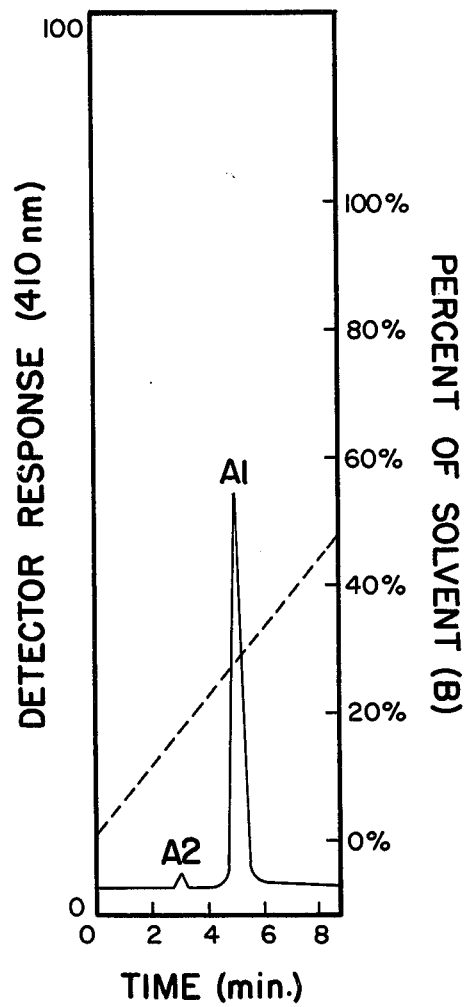
FIG. 2 is a hemoglobin profile showing resolution of a normal blood sample utilizing a DEAE Glycophase/CPG column.
Figure 3:
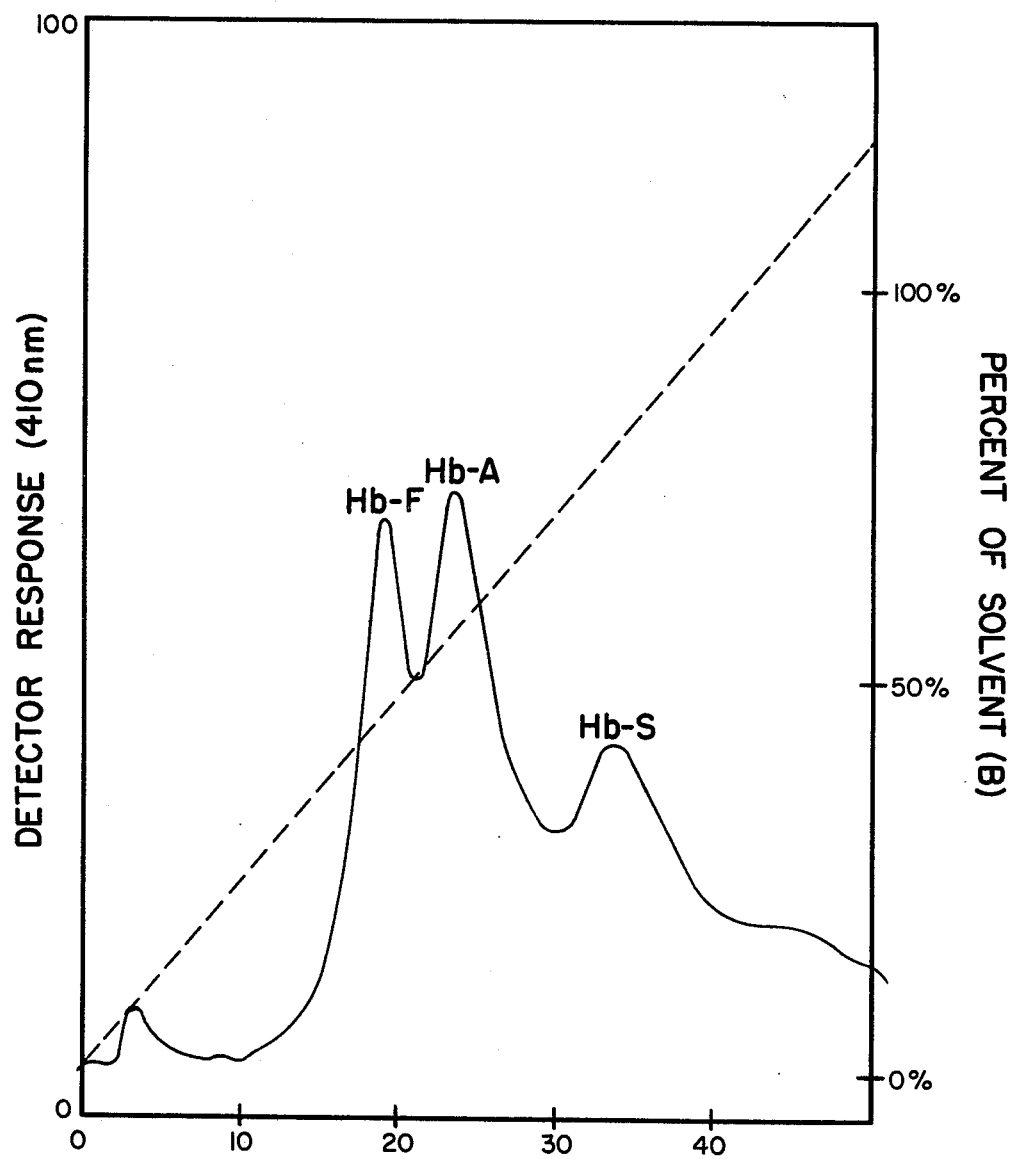
FIGS. 3 and 4 illustrate hemoglobin profiles showing resolution of hemoglobin control samples utilizing a CM Glycophase/CPG column.
Figure 4:
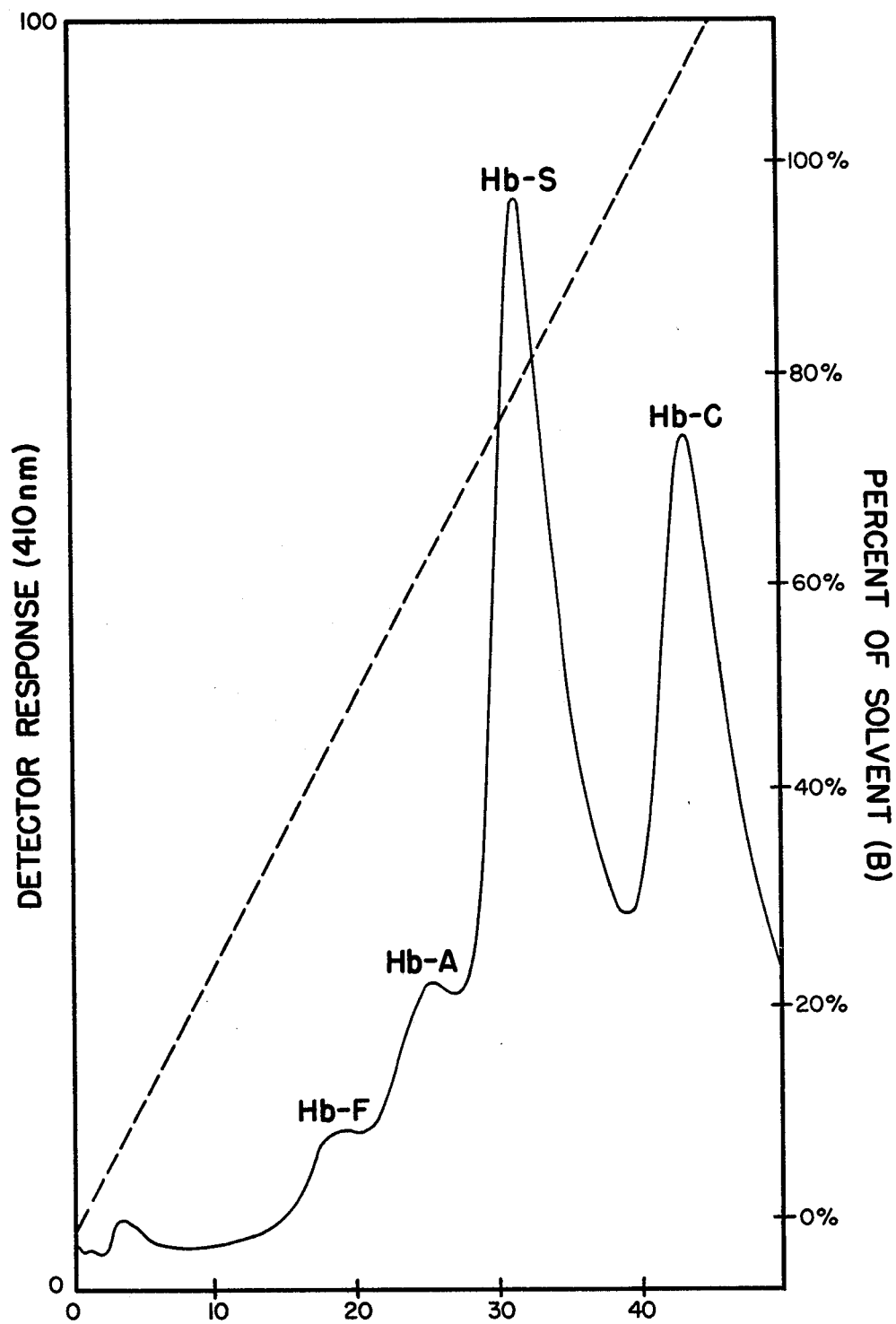

The resolution of a hemoglobin control mixture of Hb-$A_2$, Hb-S, Hb-$A_1$ and Hb-F was achieved in 6 minutes on a 5–10 μ 250 Å pore diameter DEAE Glycophase/CPG column as seen in FIG. 1. FIG. 2 shows a normal blood sample run on the same column. Hemoglobin was detected with a variable wavelength detector set at 410 nm. FIGS. 3 and 4 show the resolution of two hemoglobin control mixtures on a 5–10 μ 250 Å pore diameter CM Glycophase/CPG column. The elution time for Hb-C is 44 min. Although the analysis time on the CM column is longer than that on the DEAE, the CM analysis time may be decreased by increasing flow rate.

Glass with 250 Å pore diameter was used since it yields the optimum ion-exchange capacity for hemoglobin. Precision bore 4 × 300 mm stainless steel columns were packed using a Micromeritics column packer. This packer slurry-packs the support at about 3000 psi using the liquid chromatograph pumping system. The columns were terminated with 2 μ fritted fittings. The dimensions of the column may be altered after the initial experiments depending on the resolution requirements.

The chromatography was carried out with the protocols that have been established on gel supports. The Bis-Tris solvent system was used and appeared to be a good buffer system for cation-exchange chromatography on CM and for anion-exchange chromatography on DEAE. A small amount of KCN (0.01%) must be added to the buffers to stabilize the hemoglobins. In accordance with the dictates of the Public Health Service, it should be noted that KCN is a hazardous chemical since it releases HCN gas on reaction with acid. The buffer was therefore prepared and disposed of in the hood.

With dual columns used, the columns are run in parallel on the liquid chromatograph. The split sample elutes immediately in the void volume from one column and is resolved on the other column with a programmed gradient. By switching to the second solvent system and repeating the process, resolution occurs on the alternate column. The non-retained peak can be used to quantitate total hemoglobin, methemoglobin or cyanomethemoglobin by varying the wavelength of the spectrophotometer accordingly. Any two of these values can be determined since each sample is run twice — once on each column.

A hemoglobin control (including A, F, S, and $A_2$) was passed through a 4 × 250mm stainless steel column having a packing of DEAE Glycophase/CPG (250 Å Pore, 5–10μ) using as solvent 0.125 M Tris, pH = 8.0 (A) and 0.0125 M Tris, 0.15 M NaCl, pH = 8.0 (B) at a flow rate of 3.33 mm/sec (2.5 ml/min)under a pressure of 2200 psi. The separate hemoglobin variants (a-Hemoglobin A$_2$; b-Hemoglobin S, c-Hemoglobin A$_1$; and d-Hemoglobin F) are shown by peak identity of FIG. 1 with the detector at 410 nm. FIG. 2 shows the hemoglobin variants of a normal blood sample run under the same conditions and on the same column as that used in conjunction with the control sample shown in FIG. 1.

A hemoglobin control (including A, F and S) was passed through a 4 × 300 mm stainless steel column having a packing of CM Glyco-phase/CPG (250 Å pore, 5–10μ) using as solvent 0.03M Bis-Tris, 0.03M NaCl, 0.01% KCN at a pH = 6.1 (A) and 0.03 M Bis-Tris, 0.12 M NaCl, 0.01% KCN at a pH = 6.1 (B) at a flow rate of 1.5 mm/sec (0.7 ml/min) and at a pressure as for the DEAE Glycophase/CPG column. The separated hemoglobin variants (Hb-F, Hb-A and Hb-S) are shown by peak identity in FIG. 3.

Another hemoglobin control (including A,F,S, and C) was passed through the same column and under the same conditions as described with respect of FIG. 3. The separated hemoglobin variants (Hb-F, Hb-A and Hb-S, and Hb-C) are shown by peak identity in FIG. 4.

As can be appreciated from the foregoing, the use of high pressure liquid chromatography to analyze hemoglobin variants offers the capabilities of automation. With such a system, mass screening of the population is made possible. Total analysis requires about 30 minutes thereby making it possible to analyze numerous samples each day. Quantitation is superior to all previous methods because of elctronic data acquisition and processing so diseases such as thalassemia, which are indicated by abnormal quantities of hemoglobin variants, are more easily diagnosed. Individuals can therefore be made aware of their hemolobin profiles. Clincial manifestations of the hemoglobinopathies can then be recognized and proper precautions taken as regards surgery, pregnancy and drug administration. In addition, people can be informed of the genetic implications associated with the diseases or traits they might carry.

What is claimed is:

1. A method for rapid analysis of hemoglobin variants by high speed liquid chromatography, said method comprising:
    providing a bonded phase inorganic support at a separation area with said bonded phase being capable of separating predetermined hemoglobin variants;
    passing hemoglobin variants through said separation area and into contact with said bonded inorganic support thereat to separate said predetermined hemoglobin variants; and
    obtaining the profiles of said predetermined hemoglobin variants passed through said separation area.

2. The method of claim 1 wherein said high speed chromatography is ion-exchange chromatography, and wherein said hemoglobin variants are forced through said separation area under pressure to enable rapid separation of said variants.

3. The method of claim 2 wherein said method includes applying a pressure not greater than about 5,000 psi to cause said hemoglobin variants to be forced through said separation area.

4. The method of claim 3 wherein said rapid analysis of said hemoglobin variants requires no longer than about 30 minutes of time.

5. The method of claim 2 wherein said bonded phase support includes ion-exchange groups bonded through a carbohydrate intermediate to controlled porosity glass.

6. The method of claim 1 wherein said bonded phase support includes microparticulate support material having a particle diameter of about 5–10μ and about 250 Å pore diameter.

7. A method for rapid analysis of hemoglobin variants by high speed liquid chromatography, said method comprising:
    providing a pair of liquid chromatography columns each of which includes predetermined phases;
    passing hemoglobin variants through said columns to separate said variants;
    obtaining the profiles of hemoglobin variants separated on each of said columns; and
    combining said profiles and determining therefrom the hemoglobin variants present.

8. The method of claim 7 wherein said high speed chromatography is ion-exchange chromatography, and wherein said pair of chromatography columns are provided by preparing a first column that is an anion-exchanger and a second column that is a cation-exchanger.

9. The method of claim 8 wherein each of said columns is prepared as a bonded phase inorganic support.

10. The method of claim 9 wherein said first column is prepared by preparing a diethylaminoethanol glycophase, controlled porosity glass column and said second column is prepared by preparing a carboxymethyl glycophase, controlled porosity glass column.

11. The method of claim 7 wherein said analysis includes disease diagnosis by the presence of abnormal quantities of hemoglobin variants found to be present.

12. The method of claim 7 wherein said hemoglobin profiles are obtained by detecting and quantitating hemoglobin with a spectrophotometer at about 415 nm.

13. The method of claim 7 wherein said rapid analysis is carried out under high flow rates and pressures.

14. The method of claim 13 wherein one of said liquid chromatography columns is a diethylaminoethanol glycophase column, wherein said flow rate is about 2.5 ml/min and wherein said pressure is about 2200 psi.

15. The method of claim 13 wherein one of said liquid chromatography columns is a carboxymethyl glycophase column, and wherein said flow rate is about 0.7 ml/min and wherein said pressure is about 2200 psi.

16. A method for rapid analysis of hemoglobin variants by high speed ion-exchange chromatography, said method comprising:
    providing an anion exchanger chromatography column, said column being a diethylaminoethanol glycophase, controlled porosity glass column;
    providing a cation exchanger chromtography column, said column being a carboxymethyl glycophase, controlled porosity glass column;
    passing hemoglobin variants under pressure and at a high flow rate through each of said columns to separate said hemoglobin variants;
    detecting and quantitating said hemoglobin variants with a spectrophotometer at about 410 nm. to obtain a different hemoglobin profiles for each of said columns; and
    determining from a combination of said obtained hemoglobin profiles the relative quantities of said hemoglobin variants for diagnosis purposes.

17. The method of claim 16 wherein said method includes adding Tris or Bis-Tris as a liquid solvent to said hemoglobin passed through said columns, said liquid solvent also having NaCl and KCN added thereto.

18. The method of claim 17 wherein said liquid passed through said columns is at a pH of about 6.1.

* * * * *